(12) United States Patent
Diianni et al.

(10) Patent No.: US 12,329,928 B2
(45) Date of Patent: *Jun. 17, 2025

(54) FLUID DELIVERY DEVICE, TRANSCUTANEOUS ACCESS TOOL AND FLUID DRIVE MECHANISM FOR USE THEREWITH

(71) Applicant: Insulet Corporation, Acton, MA (US)

(72) Inventors: Steven Diianni, Danvers, MA (US); Ian McLaughlin, Groton, MA (US); Jason O'Connor, Acton, MA (US); Robert Campbell, Waltham, MA (US); Kevin Schmid, Boxford, MA (US)

(73) Assignee: Insulet Corporation, Acton, MA (US)

( * ) Notice: Subject to any disclaimer, the term of this patent is extended or adjusted under 35 U.S.C. 154(b) by 613 days.

This patent is subject to a terminal disclaimer.

(21) Appl. No.: 17/580,913

(22) Filed: Jan. 21, 2022

(65) Prior Publication Data

US 2022/0211938 A1 Jul. 7, 2022

Related U.S. Application Data

(63) Continuation of application No. 16/552,492, filed on Aug. 27, 2019, now Pat. No. 11,229,741, which is a (Continued)

(51) Int. Cl.
*A61M 5/145* (2006.01)
*A61B 5/145* (2006.01)
(Continued)

(52) U.S. Cl.
CPC ..... *A61M 5/14566* (2013.01); *A61B 5/14532* (2013.01); *A61B 5/14865* (2013.01);
(Continued)

(58) Field of Classification Search
CPC .. A61M 5/142; A61M 5/14216; A61M 5/145; A61M 5/1452; A61M 5/1456;
(Continued)

(56) References Cited

U.S. PATENT DOCUMENTS 303,013 A 8/1884 Horton
306,691 A 10/1884 Johnson
(Continued)

FOREIGN PATENT DOCUMENTS

CA 606281 A 10/1960
CN 1375338 A 10/2002
(Continued)

OTHER PUBLICATIONS

US 5,954,699 A, 09/1999, Jost et al. (withdrawn)
(Continued)

*Primary Examiner* — Kenneth J Hansen
(74) *Attorney, Agent, or Firm* — TraskBritt

(57) ABSTRACT

A fluid delivery device comprising a fluid reservoir; a transcutaneous access tool fluidly coupled to the fluid reservoir; and a drive mechanism for driving fluid from the reservoir, the drive mechanism comprising a plunger received in the reservoir; a leadscrew extending from the plunger; a nut threadably engaged with the leadscrew; a drive wheel; and a clutch mechanism coupled to the drive wheel, wherein the clutch mechanism is configured to allow the nut to pass through when disengaged and is configured to grip the nut when engaged such that the drive wheel rotates the nut to advance the drive rod and the plunger into the reservoir.

20 Claims, 6 Drawing Sheets

Related U.S. Application Data continuation of application No. 15/226,510, filed on Aug. 2, 2016, now Pat. No. 10,420,883, which is a continuation of application No. 13/854,456, filed on Apr. 1, 2013, now Pat. No. 9,402,950, which is a continuation of application No. PCT/US2013/034674, filed on Mar. 29, 2013.

(60) Provisional application No. 61/618,028, filed on Mar. 30, 2012.

(51) Int. Cl.
| | |
|---|---|
| *A61B 5/1486* | (2006.01) |
| *A61M 5/14* | (2006.01) |
| *A61M 5/142* | (2006.01) |
| *A61M 5/158* | (2006.01) |
| *A61M 5/172* | (2006.01) |
| *A61M 5/32* | (2006.01) |
| *B65D 83/00* | (2006.01) |
| *B65D 83/761* | (2025.01) |
| *F04B 9/02* | (2006.01) |

(52) U.S. Cl.
CPC .... *A61M 5/14244* (2013.01); *A61M 5/14248* (2013.01); *A61M 5/1452* (2013.01); *A61M 5/158* (2013.01); *A61M 5/1723* (2013.01); *B65D 83/761* (2025.01); *F04B 9/02* (2013.01); *A61M 2005/1403* (2013.01); *A61M 2005/14252* (2013.01); *A61M 2005/14506* (2013.01); *A61M 5/3291* (2013.01); *A61M 2230/201* (2013.01); *F04C 2270/041* (2013.01)

(58) Field of Classification Search
CPC .... A61M 5/14566; A61M 2005/14573; A61M 5/31511; A61M 5/31533; A61M 5/31535; A61M 5/31576; A61M 5/31586; F04B 9/02; B65D 83/0011; B65D 83/0027; B65D 83/0016; B05C 17/0103; B05C 17/0133; A45D 40/04
USPC .......................................... 417/319; 222/390
See application file for complete search history.

(56) References Cited

U.S. PATENT DOCUMENTS

| | | |
|---|---|---|
| 315,727 A | 4/1885 | Church |
| 405,524 A | 6/1889 | Benton. |
| 410,817 A | 9/1889 | Weeks, Jr. |
| 1,255,786 A * | 2/1918 | Phillips .............. B65D 83/0011 222/388 |
| 1,441,508 A | 1/1923 | Marius et al. |
| 2,198,666 A | 4/1940 | Gruskin |
| 2,667,986 A | 2/1954 | Perelson |
| 2,752,918 A | 7/1956 | Uytenbogaart et al. |
| 3,111,822 A | 11/1963 | Hansen |
| 3,176,712 A | 4/1965 | Ramsden |
| 3,297,260 A | 1/1967 | Barlow |
| 3,464,359 A | 9/1969 | King et al. |
| 3,505,809 A | 4/1970 | Sherwood |
| 3,631,847 A | 1/1972 | Hobbs |
| 3,792,703 A | 2/1974 | Moorehead |
| 3,812,843 A | 5/1974 | Wootten et al. |
| 3,841,328 A | 10/1974 | Jensen |
| 3,858,581 A | 1/1975 | Kamen |
| 3,885,662 A | 5/1975 | Schaefer |
| 3,946,732 A | 3/1976 | Hurscham |
| 3,947,692 A | 3/1976 | Payne |
| 3,993,061 A | 11/1976 | O'Leary |
| 3,993,226 A * | 11/1976 | Pavenick ........... B65D 83/0011 222/327 |
| 4,059,110 A | 11/1977 | Wuthrich et al. |
| 4,067,000 A | 1/1978 | Carlson |
| 4,108,177 A | 8/1978 | Pistor |
| 4,151,845 A | 5/1979 | Clemens |
| 4,152,098 A | 5/1979 | Clark et al. |
| 4,193,397 A | 3/1980 | Prosl et al. |
| 4,210,173 A | 7/1980 | Choksi et al. |
| 4,211,998 A | 7/1980 | Junginger et al. |
| 4,221,219 A | 9/1980 | Tucker |
| 4,231,019 A | 10/1980 | Junginger et al. |
| 4,248,377 A | 2/1981 | Jakobsen |
| 4,257,324 A | 3/1981 | Stefansson et al. |
| 4,261,388 A | 4/1981 | Shelton |
| 4,265,601 A | 5/1981 | Mandroian |
| 4,268,150 A | 5/1981 | Chen |
| 4,276,170 A | 6/1981 | Vaillancourt |
| 4,277,226 A | 7/1981 | Archibald |
| 4,313,439 A | 2/1982 | Babb et al. |
| 4,342,311 A | 8/1982 | Whitney et al. |
| 4,346,385 A | 8/1982 | Schiavone et al. |
| 4,364,385 A | 12/1982 | Lossef |
| 4,371,790 A | 2/1983 | Manning et al. |
| 4,373,527 A | 2/1983 | Fischell |
| 4,417,889 A | 11/1983 | Choi |
| 4,424,720 A | 1/1984 | Bucchianeri |
| 4,435,173 A | 3/1984 | Siposs et al. |
| 4,469,481 A | 9/1984 | Kobayashi |
| 4,475,901 A | 10/1984 | Kraegen et al. |
| 4,475,905 A | 10/1984 | Himmelstrup |
| 4,498,843 A | 2/1985 | Schneider et al. |
| 4,507,115 A | 3/1985 | Kambara et al. |
| 4,514,732 A | 4/1985 | Hayes, Jr. |
| 4,529,401 A | 7/1985 | Leslie et al. |
| 4,551,134 A | 11/1985 | Slavik et al. |
| 4,559,033 A | 12/1985 | Stephen et al. |
| 4,559,037 A | 12/1985 | Franetzki et al. |
| 4,560,979 A | 12/1985 | Rosskopf |
| 4,562,751 A | 1/1986 | Nason et al. |
| 4,567,549 A | 1/1986 | Lemme |
| 4,585,439 A | 4/1986 | Michel |
| 4,601,707 A | 7/1986 | Albisser et al. |
| 4,624,661 A | 11/1986 | Arimond |
| 4,634,427 A | 1/1987 | Hannula et al. |
| 4,671,429 A | 6/1987 | Spaanderman et al. |
| 4,678,408 A | 7/1987 | Nason et al. |
| 4,684,368 A | 8/1987 | Kenyon |
| 4,685,903 A | 8/1987 | Cable et al. |
| 4,734,092 A | 3/1988 | Millerd |
| 4,743,243 A | 5/1988 | Vaillancourt |
| 4,755,169 A | 7/1988 | Sarnoff et al. |
| 4,755,173 A | 7/1988 | Konopka et al. |
| 4,766,889 A | 8/1988 | Trick et al. |
| 4,781,688 A | 11/1988 | Thoma et al. |
| 4,781,693 A | 11/1988 | Martinez et al. |
| 4,801,957 A | 1/1989 | Vandemoere |
| 4,808,161 A | 2/1989 | Kamen |
| 4,836,752 A | 6/1989 | Burkett |
| 4,846,797 A | 7/1989 | Howson et al. |
| 4,855,746 A | 8/1989 | Stacy |
| 4,858,619 A | 8/1989 | Toth |
| 4,871,351 A | 10/1989 | Feingold |
| 4,882,600 A | 11/1989 | Van de Moere |
| 4,886,499 A | 12/1989 | Cirelli et al. |
| 4,898,578 A | 2/1990 | Rubalcaba, Jr. |
| 4,898,579 A | 2/1990 | Groshong et al. |
| 4,898,585 A | 2/1990 | Borsanyi et al. |
| 4,908,017 A | 3/1990 | Howson et al. |
| 4,944,659 A | 7/1990 | Labbe et al. |
| 4,969,874 A | 11/1990 | Michel et al. |
| 4,973,998 A | 11/1990 | Gates |
| 4,985,016 A | 1/1991 | Theeuwes et al. |
| 4,991,743 A | 2/1991 | Walker |
| 4,994,047 A | 2/1991 | Walker et al. |
| 5,007,458 A | 4/1991 | Marcus et al. |
| 5,020,325 A | 6/1991 | Henault |
| 5,045,871 A | 9/1991 | Reinholdson |
| 5,061,424 A | 10/1991 | Karimi et al. |
| 5,062,841 A | 11/1991 | Siegel |
| 5,097,122 A | 3/1992 | Colman et al. |
| 5,101,679 A | 4/1992 | Smith et al. |

(56) References Cited

U.S. PATENT DOCUMENTS

| | | |
|---|---|---|
| 5,109,850 A | 5/1992 | Blanco et al. |
| 5,125,415 A | 6/1992 | Bell |
| 5,147,311 A | 9/1992 | Pickhard |
| 5,176,662 A | 1/1993 | Bartholomew et al. |
| 5,178,609 A | 1/1993 | Ishikawa |
| 5,189,609 A | 2/1993 | Tivig et al. |
| 5,205,819 A | 4/1993 | Ross et al. |
| 5,213,483 A | 5/1993 | Flaherty et al. |
| 5,219,099 A | 6/1993 | Spence et al. |
| 5,222,362 A | 6/1993 | Maus et al. |
| 5,232,439 A | 8/1993 | Campbell et al. |
| 5,236,416 A | 8/1993 | McDaniel et al. |
| 5,239,326 A | 8/1993 | Takai |
| 5,244,463 A | 9/1993 | Cordner et al. |
| 5,245,447 A | 9/1993 | Stemmle |
| 5,254,096 A | 10/1993 | Rondelet et al. |
| 5,257,980 A | 11/1993 | Van et al. |
| 5,261,882 A | 11/1993 | Sealfon |
| 5,261,884 A | 11/1993 | Stern et al. |
| 5,277,338 A | 1/1994 | Divall |
| 5,281,202 A | 1/1994 | Weber et al. |
| 5,308,335 A | 5/1994 | Ross et al. |
| 5,312,337 A | 5/1994 | Flaherty et al. |
| 5,318,540 A | 6/1994 | Athayde et al. |
| 5,342,313 A | 8/1994 | Campbell et al. |
| 5,346,476 A | 9/1994 | Elson |
| 5,364,342 A | 11/1994 | Beuchat et al. |
| 5,388,615 A | 2/1995 | Edlund et al. |
| 5,411,480 A | 5/1995 | Kriesel |
| 5,433,710 A | 7/1995 | Vanantwerp et al. |
| 5,452,033 A | 9/1995 | Balling et al. |
| 5,492,534 A | 2/1996 | Athayde et al. |
| 5,503,628 A | 4/1996 | Fetters et al. |
| 5,505,709 A | 4/1996 | Funderburk et al. |
| 5,507,288 A | 4/1996 | Boecker et al. |
| 5,514,096 A | 5/1996 | Hiejima |
| 5,520,661 A | 5/1996 | Lal et al. |
| 5,533,389 A | 7/1996 | Kamen et al. |
| 5,545,152 A | 8/1996 | Funderburk et al. |
| 5,573,342 A | 11/1996 | Patalano |
| 5,575,770 A | 11/1996 | Melsky et al. |
| 5,576,781 A | 11/1996 | Deleeuw |
| 5,582,593 A | 12/1996 | Hultman |
| 5,584,813 A | 12/1996 | Livingston et al. |
| 5,613,956 A | 3/1997 | Patterson et al. |
| 5,618,269 A | 4/1997 | Jacobsen et al. |
| 5,628,309 A | 5/1997 | Brown |
| 5,630,710 A | 5/1997 | Tune et al. |
| 5,637,095 A | 6/1997 | Nason et al. |
| 5,643,213 A | 7/1997 | McPhee |
| 5,647,853 A | 7/1997 | Feldmann et al. |
| 5,665,065 A | 9/1997 | Colman et al. |
| 5,665,070 A | 9/1997 | McPhee |
| 5,685,859 A | 11/1997 | Kornerup |
| 5,693,018 A | 12/1997 | Kriesel et al. |
| 5,695,474 A | 12/1997 | Daugherty |
| 5,695,490 A | 12/1997 | Flaherty et al. |
| 5,702,363 A | 12/1997 | Flaherty |
| 5,704,520 A | 1/1998 | Gross |
| 5,713,875 A | 2/1998 | Tanner, II |
| 5,716,343 A | 2/1998 | Kriesel et al. |
| 5,726,404 A | 3/1998 | Brody |
| 5,726,751 A | 3/1998 | Altendorf et al. |
| 5,741,228 A | 4/1998 | Lambrecht et al. |
| 5,747,350 A | 5/1998 | Sattler |
| 5,748,827 A | 5/1998 | Holl et al. |
| 5,755,682 A | 5/1998 | Knudson et al. |
| 5,764,159 A | 6/1998 | Neftel |
| 5,776,103 A | 7/1998 | Kriesel et al. |
| 5,779,676 A | 7/1998 | Kriesel et al. |
| 5,785,681 A | 7/1998 | Indravudh |
| 5,785,688 A | 7/1998 | Joshi et al. |
| 5,797,881 A | 8/1998 | Gadot |
| 5,800,397 A | 9/1998 | Wilson et al. |
| 5,800,405 A | 9/1998 | Mcphee |
| 5,800,420 A | 9/1998 | Gross et al. |
| 5,807,075 A | 9/1998 | Jacobsen et al. |
| 5,810,015 A | 9/1998 | Flaherty |
| 5,814,020 A | 9/1998 | Gross |
| 5,839,467 A | 11/1998 | Saaski et al. |
| 5,840,063 A | 11/1998 | Flaherty |
| 5,845,218 A | 12/1998 | Altschul |
| 5,848,990 A | 12/1998 | Cirelli et al. |
| 5,848,991 A | 12/1998 | Gross et al. |
| 5,851,197 A | 12/1998 | Marano et al. |
| 5,858,005 A | 1/1999 | Kriesel |
| 5,858,239 A | 1/1999 | Kenley et al. |
| 5,865,806 A | 2/1999 | Howell |
| 5,871,470 A | 2/1999 | McWha |
| 5,875,393 A | 2/1999 | Altschul et al. |
| 5,878,539 A | 3/1999 | Grubb |
| 5,885,659 A | 3/1999 | Takahashi et al. |
| 5,885,808 A | 3/1999 | Spooner et al. |
| 5,886,647 A | 3/1999 | Badger et al. |
| 5,891,097 A | 4/1999 | Saito et al. |
| 5,897,530 A | 4/1999 | Jackson |
| 5,906,597 A | 5/1999 | McPhee |
| 5,911,716 A | 6/1999 | Rake et al. |
| 5,919,167 A | 7/1999 | Mulhauser et al. |
| 5,921,419 A | 7/1999 | Niedospial et al. |
| 5,931,814 A | 8/1999 | Alex et al. |
| 5,935,099 A | 8/1999 | Peterson et al. |
| 5,954,058 A | 9/1999 | Flaherty |
| 5,954,694 A | 9/1999 | Sunseri |
| 5,957,859 A | 9/1999 | Rosenfeld |
| 5,957,890 A | 9/1999 | Mann et al. |
| 5,961,492 A | 10/1999 | Kriesel et al. |
| 5,965,848 A | 10/1999 | Altschul et al. |
| 5,971,963 A | 10/1999 | Choi |
| 5,983,094 A | 11/1999 | Altschul et al. |
| 5,993,423 A | 11/1999 | Choi |
| 5,997,501 A | 12/1999 | Gross et al. |
| 6,019,747 A | 2/2000 | McPhee |
| 6,024,539 A | 2/2000 | Blomquist |
| 6,050,457 A | 4/2000 | Arnold et al. |
| 6,050,978 A | 4/2000 | Orr et al. |
| 6,068,615 A | 5/2000 | Brown et al. |
| 6,071,292 A | 6/2000 | Makower et al. |
| 6,074,369 A | 6/2000 | Sage et al. |
| 6,086,615 A | 7/2000 | Wood et al. |
| 6,090,092 A | 7/2000 | Fowles et al. |
| 6,126,637 A | 10/2000 | Kriesel et al. |
| 6,144,847 A | 11/2000 | Altschul et al. |
| 6,152,898 A | 11/2000 | Olsen |
| 6,159,188 A | 12/2000 | Laibovitz et al. |
| 6,174,300 B1 | 1/2001 | Kriesel et al. |
| 6,190,359 B1 | 2/2001 | Heruth |
| 6,200,293 B1 | 3/2001 | Kriesel et al. |
| 6,200,338 B1 | 3/2001 | Solomon et al. |
| 6,206,850 B1 | 3/2001 | O'Neil |
| 6,244,776 B1 | 6/2001 | Wiley |
| 6,244,778 B1 | 6/2001 | Chesbrough |
| 6,309,370 B1 | 10/2001 | Haim et al. |
| 6,352,522 B1 | 3/2002 | Kim et al. |
| 6,363,609 B1 | 4/2002 | Pickren |
| 6,375,638 B2 | 4/2002 | Nason et al. |
| 6,375,639 B1 | 4/2002 | Duplessie et al. |
| 6,413,244 B1 | 7/2002 | Bestetti et al. |
| 6,474,219 B2 | 11/2002 | Klitmose et al. |
| 6,475,196 B1 | 11/2002 | Vachon |
| 6,485,461 B1 | 11/2002 | Mason et al. |
| 6,485,462 B1 | 11/2002 | Kriesel |
| 6,488,652 B1 | 12/2002 | Weijand et al. |
| 6,520,936 B1 | 2/2003 | Mann |
| 6,527,744 B1 | 3/2003 | Kriesel et al. |
| 6,537,249 B2 | 3/2003 | Kriesell et al. |
| 6,539,286 B1 | 3/2003 | Jiang |
| 6,569,115 B1 | 5/2003 | Barker et al. |
| 6,569,125 B2 | 5/2003 | Jepson et al. |
| 6,572,542 B1 | 6/2003 | Houben et al. |
| 6,572,585 B2 | 6/2003 | Choi |
| 6,595,956 B1 | 7/2003 | Gross et al. |
| 6,656,158 B2 | 12/2003 | Mahoney et al. |
| 6,666,852 B2 | 12/2003 | Niedospial, Jr. |

(56) References Cited

U.S. PATENT DOCUMENTS

| | | |
|---|---|---|
| 6,699,218 B2 | 3/2004 | Flaherty et al. |
| 6,699,221 B2 | 3/2004 | Vaillancourt |
| 6,723,072 B2 | 4/2004 | Flaherty et al. |
| 6,740,059 B2 | 5/2004 | Flaherty |
| 6,749,407 B2 | 6/2004 | Xie et al. |
| 6,851,260 B2 | 2/2005 | Morten |
| 6,883,778 B1 | 4/2005 | Newton et al. |
| 7,008,404 B2 | 3/2006 | Nakajima |
| 7,018,360 B2 | 3/2006 | Flaherty et al. |
| 7,025,744 B2 | 4/2006 | Utterberg et al. |
| 7,060,059 B2 | 6/2006 | Keith et al. |
| 7,104,275 B2 | 9/2006 | Dille |
| 7,128,727 B2 | 10/2006 | Flaherty et al. |
| 7,137,964 B2 | 11/2006 | Flaherty |
| 7,144,384 B2 | 12/2006 | Gorman et al. |
| 7,160,272 B1 | 1/2007 | Eyal et al. |
| 7,267,665 B2 | 9/2007 | Steil et al. |
| 7,291,133 B1 | 11/2007 | Kindler et al. |
| 7,303,549 B2 | 12/2007 | Flaherty et al. |
| 7,771,392 B2 | 8/2010 | De et al. |
| 7,785,296 B2 | 8/2010 | Muskatello et al. |
| 7,914,499 B2 | 3/2011 | Gonnelli et al. |
| 7,918,825 B2 | 4/2011 | O'Connor et al. |
| 7,951,114 B2 | 5/2011 | Rush et al. |
| 8,267,921 B2 | 9/2012 | Yodfat et al. |
| 8,382,703 B1 | 2/2013 | Abdelaal |
| 8,499,913 B2 | 8/2013 | Gunter |
| 8,905,995 B2 | 12/2014 | Mernoe |
| 8,920,376 B2 | 12/2014 | Caffey et al. |
| 8,939,935 B2 | 1/2015 | O'Connor et al. |
| 9,180,244 B2 | 11/2015 | Anderson et al. |
| 9,192,716 B2 | 11/2015 | Jugl et al. |
| 9,402,950 B2 | 8/2016 | Dilanni et al. |
| 9,539,596 B2 | 1/2017 | Ikushima |
| 10,441,723 B2 | 10/2019 | Nazzaro |
| 10,695,485 B2 | 6/2020 | Nazzaro |
| 2001/0016710 A1 | 8/2001 | Nason et al. |
| 2001/0056258 A1 | 12/2001 | Evans |
| 2002/0010423 A1 | 1/2002 | Gross et al. |
| 2002/0029018 A1 | 3/2002 | Jeffrey |
| 2002/0032374 A1 | 3/2002 | Holker et al. |
| 2002/0037221 A1 | 3/2002 | Mastrangelo et al. |
| 2002/0173769 A1 | 11/2002 | Gray et al. |
| 2002/0173830 A1 | 11/2002 | Starkweather et al. |
| 2003/0040715 A1 | 2/2003 | D'Antonio et al. |
| 2003/0055380 A1 | 3/2003 | Flaherty |
| 2003/0097092 A1 | 5/2003 | Flaherty |
| 2003/0109827 A1 | 6/2003 | Lavi et al. |
| 2003/0163097 A1 | 8/2003 | Fleury et al. |
| 2003/0198558 A1 | 10/2003 | Nason et al. |
| 2003/0199825 A1 | 10/2003 | Flaherty |
| 2004/0010207 A1 | 1/2004 | Flaherty et al. |
| 2004/0068224 A1 | 4/2004 | Couvillon et al. |
| 2004/0069044 A1 | 4/2004 | Lavi et al. |
| 2004/0087904 A1 | 5/2004 | Langley et al. |
| 2004/0088224 A1 | 5/2004 | Mukai |
| 2004/0092865 A1 | 5/2004 | Flaherty et al. |
| 2004/0094733 A1 | 5/2004 | Hower et al. |
| 2004/0115068 A1 | 6/2004 | Hansen et al. |
| 2004/0116847 A1 | 6/2004 | Wall |
| 2004/0153032 A1 | 8/2004 | Garribotto et al. |
| 2004/0158208 A1 | 8/2004 | Hiejima |
| 2004/0160437 A1 | 8/2004 | Onozawa et al. |
| 2004/0203357 A1 | 10/2004 | Nassimi |
| 2005/0020980 A1 | 1/2005 | Inoue et al. |
| 2005/0165363 A1 | 7/2005 | Judson et al. |
| 2005/0187524 A1 | 8/2005 | Willis et al. |
| 2005/0238507 A1 | 10/2005 | Diianni et al. |
| 2005/0258581 A1 | 11/2005 | Tanaka |
| 2005/0273059 A1 | 12/2005 | Mernoe et al. |
| 2005/0277882 A1 | 12/2005 | Kriesel |
| 2006/0041229 A1 | 2/2006 | Garibotto et al. |
| 2006/0079765 A1 | 4/2006 | Neer et al. |
| 2006/0134323 A1 | 6/2006 | O'Brien |
| 2006/0155210 A1 | 7/2006 | Beckman et al. |
| 2006/0173439 A1 | 8/2006 | Thorne et al. |
| 2006/0178633 A1 | 8/2006 | Garibotto et al. |
| 2006/0204535 A1 | 9/2006 | Johnson |
| 2006/0253085 A1 | 11/2006 | Geismar et al. |
| 2006/0282290 A1 | 12/2006 | Flaherty et al. |
| 2007/0005018 A1 | 1/2007 | Tekbuchava |
| 2007/0025811 A1 | 2/2007 | Wilhelm |
| 2007/0073236 A1 | 3/2007 | Mernoe et al. |
| 2007/0088271 A1 | 4/2007 | Richards |
| 2007/0112332 A1 | 5/2007 | Harding et al. |
| 2007/0118405 A1 | 5/2007 | Campbell et al. |
| 2007/0129690 A1 | 6/2007 | Rosenblatt et al. |
| 2007/0173974 A1 | 7/2007 | Lin |
| 2007/0197163 A1 | 8/2007 | Robertson |
| 2007/0282269 A1 | 12/2007 | Carter et al. |
| 2008/0004515 A1 | 1/2008 | Jennewine |
| 2008/0006500 A1 | 1/2008 | Spahr |
| 2008/0007141 A1 | 1/2008 | Deck |
| 2008/0051738 A1 | 2/2008 | Griffin |
| 2008/0065050 A1 | 3/2008 | Sparks et al. |
| 2008/0078400 A1 | 4/2008 | Martens et al. |
| 2008/0114304 A1 | 5/2008 | Nalesso et al. |
| 2008/0132880 A1 | 6/2008 | Buchman |
| 2008/0172028 A1 | 7/2008 | Blomquist |
| 2008/0183060 A1 | 7/2008 | Steil et al. |
| 2008/0243211 A1 | 10/2008 | Cartwright et al. |
| 2008/0249508 A1 | 10/2008 | Lopez et al. |
| 2008/0287906 A1 | 11/2008 | Burkholz et al. |
| 2008/0294040 A1 | 11/2008 | Mohiuddin et al. |
| 2009/0024083 A1 | 1/2009 | Kriesel et al. |
| 2009/0054866 A1 | 2/2009 | Teisen-Simony et al. |
| 2009/0062767 A1 | 3/2009 | Van et al. |
| 2009/0069787 A1 | 3/2009 | Estes et al. |
| 2009/0099521 A1 | 4/2009 | Gravesen et al. |
| 2009/0124979 A1 | 5/2009 | Raymond et al. |
| 2009/0124994 A1 | 5/2009 | Roe |
| 2009/0198215 A1 | 8/2009 | Chong et al. |
| 2009/0278875 A1 | 11/2009 | Holm et al. |
| 2009/0299300 A1 | 12/2009 | Truitt et al. |
| 2009/0326472 A1 | 12/2009 | Carter et al. |
| 2010/0036326 A1 | 2/2010 | Matusch |
| 2010/0137784 A1 | 6/2010 | Cefai et al. |
| 2010/0145272 A1 | 6/2010 | Cefai et al. |
| 2010/0152658 A1 | 6/2010 | Hanson et al. |
| 2010/0241066 A1 | 9/2010 | Hansen et al. |
| 2010/0241086 A1 | 9/2010 | Yodfat et al. |
| 2011/0054390 A1 | 3/2011 | Searle et al. |
| 2011/0054399 A1 | 3/2011 | Chong et al. |
| 2011/0073620 A1 | 3/2011 | Verrilli |
| 2011/0144586 A1 | 6/2011 | Michaud et al. |
| 2011/0166512 A1 | 7/2011 | Both et al. |
| 2011/0180480 A1 | 7/2011 | Kloeffel et al. |
| 2011/0213329 A1 | 9/2011 | Yodfat et al. |
| 2011/0230833 A1 | 9/2011 | Landman et al. |
| 2011/0251509 A1 | 10/2011 | Beyhan et al. |
| 2011/0316562 A1 | 12/2011 | Cefai et al. |
| 2012/0003093 A1 | 1/2012 | Lischer et al. |
| 2012/0003935 A1 | 1/2012 | Lydon et al. |
| 2012/0010594 A1 | 1/2012 | Holt et al. |
| 2012/0078161 A1 | 3/2012 | Masterson et al. |
| 2012/0109066 A1 | 5/2012 | Chase et al. |
| 2012/0172817 A1 | 7/2012 | Bruggemann et al. |
| 2012/0209207 A1 | 8/2012 | Gray et al. |
| 2012/0238851 A1 | 9/2012 | Kamen et al. |
| 2012/0277668 A1 | 11/2012 | Chawla |
| 2013/0006213 A1 | 1/2013 | Arnitz et al. |
| 2013/0017099 A1 | 1/2013 | Genoud et al. |
| 2013/0060233 A1 | 3/2013 | O'Connor et al. |
| 2013/0064701 A1 | 3/2013 | Konishi |
| 2013/0177455 A1 | 7/2013 | Kamen et al. |
| 2013/0178791 A1 | 7/2013 | Javitt |
| 2013/0178803 A1 | 7/2013 | Raab |
| 2013/0245545 A1 | 9/2013 | Arnold et al. |
| 2013/0267932 A1 | 10/2013 | Franke et al. |
| 2013/0296792 A1 | 11/2013 | Cabiri |
| 2013/0317753 A1 | 11/2013 | Kamen et al. |
| 2014/0018730 A1 | 1/2014 | Mueller-Pathle |
| 2014/0066859 A1 | 3/2014 | Ogawa et al. |
| 2014/0074033 A1 | 3/2014 | Sonderegger et al. |

(56) References Cited

U.S. PATENT DOCUMENTS

| | | |
|---|---|---|
| 2014/0127048 A1 | 5/2014 | Diianni et al. |
| 2014/0128839 A1 | 5/2014 | Diianni et al. |
| 2014/0135880 A1 | 5/2014 | Baumgartner et al. |
| 2014/0142508 A1 | 5/2014 | Diianni et al. |
| 2014/0148784 A1 | 5/2014 | Anderson et al. |
| 2014/0171901 A1 | 6/2014 | Langsdorf et al. |
| 2014/0316379 A1 | 10/2014 | Sonderegger et al. |
| 2015/0041498 A1 | 2/2015 | Kakiuchi et al. |
| 2015/0051487 A1 | 2/2015 | Uber et al. |
| 2015/0057613 A1 | 2/2015 | Clemente et al. |
| 2015/0064036 A1 | 3/2015 | Eberhard |
| 2015/0137017 A1 | 5/2015 | Ambrosina et al. |
| 2015/0202386 A1 | 7/2015 | Brady et al. |
| 2015/0290389 A1 | 10/2015 | Nessel |
| 2015/0297825 A1 | 10/2015 | Focht et al. |
| 2016/0008549 A1 | 1/2016 | Plumptre et al. |
| 2016/0015891 A1 | 1/2016 | Papiorek |
| 2016/0025544 A1 | 1/2016 | Kamen et al. |
| 2016/0038689 A1 | 2/2016 | Lee et al. |
| 2016/0055842 A1 | 2/2016 | DeFranks et al. |
| 2016/0082242 A1 | 3/2016 | Burton et al. |
| 2016/0129190 A1 | 5/2016 | Haitsuka |
| 2016/0193423 A1 | 7/2016 | Bilton |
| 2016/0213851 A1 | 7/2016 | Weibel et al. |
| 2016/0302054 A1 | 10/2016 | Kimura et al. |
| 2017/0021096 A1 | 1/2017 | Cole et al. |
| 2017/0021137 A1 | 1/2017 | Cole |
| 2017/0100541 A1 | 4/2017 | Constantineau et al. |
| 2017/0128664 A1 | 5/2017 | Diianni et al. |
| 2017/0216516 A1 | 8/2017 | Dale et al. |
| 2017/0239415 A1 | 8/2017 | Hwang et al. |
| 2017/0290975 A1 | 10/2017 | Barmaimon et al. |
| 2018/0021521 A1 | 1/2018 | Sanchez |
| 2018/0185579 A1 | 7/2018 | Joseph et al. |
| 2018/0313346 A1 | 11/2018 | Oakes et al. |
| 2019/0151547 A1 | 5/2019 | Cowe et al. |
| 2019/0192782 A1 | 6/2019 | Pedersen et al. |
| 2019/0365993 A1 | 12/2019 | Staub et al. |
| 2020/0009315 A1 | 1/2020 | Brouet et al. |
| 2020/0345931 A1 | 11/2020 | Gray et al. |

FOREIGN PATENT DOCUMENTS

| | | |
|---|---|---|
| CN | 102498292 B | 7/2015 |
| CN | 204972511 U | 1/2016 |
| CN | 105764543 B | 7/2016 |
| CN | 206175149 U | 5/2017 |
| CN | 107096091 A | 8/2017 |
| CN | 108472441 A | 8/2018 |
| DE | 0420595 C | 10/1925 |
| DE | 4200595 A1 | 7/1993 |
| DE | 19723648 C1 | 8/1998 |
| DE | 19920896 A1 | 11/2000 |
| DE | 102005040344 A1 | 3/2007 |
| EP | 0341049 A2 | 11/1989 |
| EP | 0342947 A2 | 11/1989 |
| EP | 0454331 A1 | 10/1991 |
| EP | 0496305 A2 | 7/1992 |
| EP | 0338806 B1 | 2/1994 |
| EP | 0763369 A1 | 3/1997 |
| EP | 0789146 A1 | 8/1997 |
| EP | 0867196 A2 | 9/1998 |
| EP | 0937475 A2 | 8/1999 |
| EP | 1065378 A2 | 1/2001 |
| EP | 1403519 A1 | 3/2004 |
| EP | 1177802 B1 | 9/2004 |
| EP | 1501573 A2 | 2/2005 |
| EP | 2397181 A1 | 12/2011 |
| EP | 2468338 A1 | 6/2012 |
| EP | 2703024 A1 | 3/2014 |
| EP | 1874390 B1 | 10/2014 |
| EP | 2830499 A1 | 2/2015 |
| FR | 2096275 A5 | 2/1972 |
| FR | 2455269 A1 | 11/1980 |
| FR | 2507637 A1 | 12/1982 |
| FR | 2731475 A1 | 9/1996 |
| GB | 0357139 A | 9/1931 |
| GB | 0810488 A | 3/1959 |
| GB | 0875034 A | 8/1961 |
| GB | 1204836 A | 9/1970 |
| GB | 2008806 A | 6/1979 |
| GB | 2077367 A | 12/1981 |
| GB | 2224444 A | 5/1990 |
| GB | 2443261 A | 4/2008 |
| GB | 2456681 A | 7/2009 |
| GB | 2463051 A | 3/2010 |
| GB | 2549750 A | 11/2017 |
| IL | 46017 A | 11/1977 |
| JP | 06-063133 A | 3/1994 |
| JP | 06-296690 A | 10/1994 |
| JP | 08-238324 A | 9/1996 |
| JP | 2004-247271 A | 9/2004 |
| JP | 2004-274719 A | 9/2004 |
| JP | 2005-188355 A | 7/2005 |
| JP | 2006-159228 A | 6/2006 |
| JP | 2006-249130 A | 9/2006 |
| JP | 2009514580 A | 4/2009 |
| JP | 6098988 B2 | 3/2017 |
| JP | 2017513577 A | 6/2017 |
| NL | 1019126 C1 | 4/2003 |
| TW | 200740148 A | 10/2007 |
| TW | M452390 U | 5/2013 |
| WO | 81/01658 A1 | 6/1981 |
| WO | 86/06796 A1 | 11/1986 |
| WO | 93/20864 A1 | 10/1993 |
| WO | 94/15660 A1 | 7/1994 |
| WO | 98/00193 A1 | 1/1998 |
| WO | 98/01071 A1 | 1/1998 |
| WO | 98/55073 A1 | 12/1998 |
| WO | 98/56293 A1 | 12/1998 |
| WO | 99/10040 A1 | 3/1999 |
| WO | 99/10049 A1 | 3/1999 |
| WO | 99/56803 A1 | 11/1999 |
| WO | 99/62576 A1 | 12/1999 |
| WO | 00/19887 A1 | 4/2000 |
| WO | 00/29047 A1 | 5/2000 |
| WO | 00/29049 A1 | 5/2000 |
| WO | 00/30705 A1 | 6/2000 |
| WO | 00/61215 A1 | 10/2000 |
| WO | 00/74752 A1 | 12/2000 |
| WO | 00/78210 A1 | 12/2000 |
| WO | 01/05663 A2 | 1/2001 |
| WO | 01/52727 A1 | 7/2001 |
| WO | 01/56633 A2 | 8/2001 |
| WO | 01/72354 A2 | 10/2001 |
| WO | 01/76684 A1 | 10/2001 |
| WO | 01/78812 A1 | 10/2001 |
| WO | 02/15954 A1 | 2/2002 |
| WO | 02/20073 A2 | 3/2002 |
| WO | 02/26282 A2 | 4/2002 |
| WO | 02/40083 A2 | 5/2002 |
| WO | 02/68823 A1 | 9/2002 |
| WO | 02/76535 A1 | 10/2002 |
| WO | 03/30984 A1 | 4/2003 |
| WO | 03/59420 A1 | 7/2003 |
| WO | 03/90509 A2 | 11/2003 |
| WO | 03/97133 A1 | 11/2003 |
| WO | 2004/032994 A2 | 4/2004 |
| WO | 2004/056412 A2 | 7/2004 |
| WO | 2004/110526 A1 | 12/2004 |
| WO | 2006/053007 A2 | 5/2006 |
| WO | 2006/086201 A2 | 8/2006 |
| WO | 2007/064835 A2 | 6/2007 |
| WO | 2007/066152 A2 | 6/2007 |
| WO | 2008/024810 A2 | 2/2008 |
| WO | 2008/133702 A1 | 11/2008 |
| WO | 2009/039203 A2 | 3/2009 |
| WO | 2009/068251 A1 | 6/2009 |
| WO | 2009/098648 A2 | 8/2009 |
| WO | 2009/141005 A1 | 11/2009 |
| WO | 2010022069 A2 | 2/2010 |
| WO | 2010055504 A1 | 5/2010 |
| WO | 2010077279 A1 | 7/2010 |
| WO | 2010/089418 A2 | 8/2010 |

(56) References Cited

FOREIGN PATENT DOCUMENTS

| | | | |
|---|---|---|---|
| WO | 2010/139793 A1 | 12/2010 |
| WO | 2011/010198 A2 | 1/2011 |
| WO | 2011031458 A1 | 3/2011 |
| WO | 2011/069935 A2 | 6/2011 |
| WO | 2011/075042 A1 | 6/2011 |
| WO | 2011/095483 A1 | 8/2011 |
| WO | 2011/133823 A1 | 10/2011 |
| WO | 2012/045667 A2 | 4/2012 |
| WO | 2012/073032 A1 | 6/2012 |
| WO | 2012/108959 A1 | 8/2012 |
| WO | 2012/134588 A1 | 10/2012 |
| WO | 2012/134589 A1 | 10/2012 |
| WO | 2013/050535 A2 | 4/2013 |
| WO | 2013/078200 A1 | 5/2013 |
| WO | 2013/134486 A2 | 9/2013 |
| WO | 2013/137893 A1 | 9/2013 |
| WO | 2013149186 A1 | 10/2013 |
| WO | 2013/182321 A1 | 12/2013 |
| WO | 2014029416 A1 | 2/2014 |
| WO | 2014/099404 A1 | 6/2014 |
| WO | 2014/149357 A1 | 9/2014 |
| WO | 2014179774 A1 | 11/2014 |
| WO | 2014/194183 A2 | 12/2014 |
| WO | 2015/032772 A1 | 3/2015 |
| WO | 2015/061493 A1 | 4/2015 |
| WO | 2015048791 A1 | 4/2015 |
| WO | 2015/081337 A2 | 6/2015 |
| WO | 2015/117854 A1 | 8/2015 |
| WO | 2015/167201 A1 | 11/2015 |
| WO | 2015/177082 A1 | 11/2015 |
| WO | 2016/141082 A1 | 9/2016 |
| WO | 2017/148855 A1 | 9/2017 |
| WO | 2017/187177 A1 | 11/2017 |
| WO | 2017/205816 A1 | 11/2017 |
| WO | 2021016452 A1 | 1/2021 |

OTHER PUBLICATIONS

International Search Report and Written Opinion for International Patent Application No. PCT/US2022/029012, mailed Aug. 19, 2022, 12 pages.
International Search Report and Written Opinion, Application No. PCT/US2022/016713, mailed Aug. 5, 2022, 19 pages.
International Search Report and Written Opinion for International Patent Application No. PCT/US2022/011356, dated Apr. 29, 2022, 19 pages.
International Search Report and Written Opinion for the International Patent Application No. PCT/US2021/055581, dated Feb. 8, 2022, 19 pages.
U.S. Office Action dated Mar. 3, 2017, issued in U.S. Appl. No. 13/854,463, 11 pages.
U.S. Office Action dated Mar. 31, 2015, issued in U.S. Appl. No. 13/854,456, 10 pages.
U.S. Office Action dated May 17, 2016, issued in U.S. Appl. No. 13/854,445, 10 pages.
U.S. Office Action dated Oct. 31, 2017, issued in U.S. Appl. No. 13/854,445, 14 pages.
U.S. Office Action dated Oct. 31, 2017, issued in U.S. Appl. No. 13/854,463 13 pages.
U.S. Office Action dated Sep. 23, 2015, issued in U.S. Appl. No. 13/854,456, 13 pages.
User's Guide for Model 508 Insulin Pump, Mini Med, Aug. 2000, 145 pages.
Vaughan, M.E., ""The Design, Fabrication, and Modeling of a Piezoelectric Linear Motor."" Master's thesis, Virginia Polytechnic Institute and State University, VA. (2001).
Web-Site Brochure dated Dec. 20, 1999. "The Animas R-1000 Insulin Pump", www.animascorp.com/pump_f_ s.html.
Web-Site Brochure dated Dec. 20, 1999. Applied Medical Technology. "508 Pump Information", www.applied-medical.co.uk/508.htm.
Web-Site Brochure dated Jan. 4, 2000. MiniMed 508. "Doing its job. Naturally." www.minimed.com/files/mm113.htm.
Web-Site Brochure dated Jan. 4, 2000. SOOIL-Homepage. "Portable Insulin Pump", www.sooil.com/product2.htm.
"Lind, et al. "Linear Motion Miniature Actuators."" Paper presented at the 2nd Tampere International Conference on Machine Automation, Tampere, Finland (Sep. 1998), 12 pages.
Author unknown, "The Animas R-1000 Insulin Pump—Animas Corporation intends to exit the insulin pump business and discontinue the manufacturing and sale of Animas Vibe and One Touch Ping insulin pumps." [online], Dec. 1999 [retrieved on Jan. 8, 2019], Retrieved from the Internet URL: http://www.animaspatientsupport.com/ using the Wayback Machine.
Author unknown, CeramTec ""Discover the Electro Ceramic Products CeramTec acquired from Morgan AdvancedMaterials"" [online], Mar. 1, 2001 [retrieved on Jan. 8, 2019. Retrieved from the Internet URL: http://www.rnorgantechnicalceramics.com/.
EPO Search Report dated Nov. 11, 2015, received in corresponding Application No. 13768938.6, 7 pgs.
European Communication pursuant to Article 94(3) EPC for European Application No. 19157933.3, dated Apr. 30, 2020, 3 pages.
European Communication pursuant to Article 94(3) EPC for European Application No. 19157933.3, dated Mar. 18, 2021, 4 pages.
European Communication pursuant to Article 94(3) EPC for European Application No. 19157933.3, dated Oct. 1, 2021, 3 pages.
European Search Report and Written Opinion for the European Patent Application No. EP19177571, dated Oct. 30, 2019, 8 pages.
European Search Report and Written Opinion for the European Patent Application No. EP20174878, dated Sep. 29, 2020, 3 pages.
Extended European Search Report and Search Opinion Received for EP Application No. 19157933.3, dated on Jul. 2, 2019, 6 pages.
Extended European Search Report and Search Opinion Received for EP Application No. 23152851.4, dated on May 31, 2023, 7 pages.
Extended European Search Report and Search Opinion Received for EP Application No. 24181903.6, dated on Sep. 16, 2024, 7 pages.
Galante, et al., "Design, Modeling, and Performance of a High Force Piezoelectric Inchworm Motor," Journal of Intelligent Material Systems and Structures, vol. 10, 962-972 (1999).
International Preliminary Report on Patentability dated Apr. 9, 2020, issued in PCT Patent Application No. PCT/US2018/052464, 7 pages.
International Preliminary Report on Patentability dated Oct. 1, 2014, issued in PCT Patent Application No. PCT/US2013/034674, 15 pages.
International Preliminary Report on Patentability for International application No. PCT/US2017/034811 dated Nov. 27, 2018 10 pages.
International Preliminary Report on Patentability for the International Patent Application No. PCT/US18/14351, dated Jul. 23, 2019, 6 pages.
International Preliminary Report on Patentability for the International Patent Application No. PCT/US2017/046508 dated Feb. 12, 2019 10 pp.
International Preliminary Report on Patentability for the International Patent Application No. PCT/US2017/046737, dated Feb. 19, 2019, 8 pages.
International Preliminary Report on Patentability for the International Patent Application No. PCT/US2017/055054, dated Apr. 9, 2019, 8 pages.
International Preliminary Report on Patentability for the International Patent Application No. PCT/US2018/045155, dated Feb. 4, 2020, 10 pages.
International Preliminary Reporton Patentability for the International Patent Application No. PCT/US2017/046777, dated Feb. 19, 2019, 8 pages.
International Search Report and the Written Opinion of the International Searching Authority in PCT Application No. PCT/GB2015/050248, dated Jun. 23, 2015, 11 pages.
International Search Report and Written Opinion for application No. PCT/US18/52464, dated Jan. 4, 2019, 11 pages.
International Search Report and Written Opinion for application No. PCT/US2017/015601, dated May 16, 2017, 12 pages.
International Search Report and Written Opinion for application No. PCT/US2017/034811, dated Oct. 18, 2017, 15 pages.

(56) References Cited

OTHER PUBLICATIONS

International Search Report and Written Opinion for Application No. PCT/US2019/059854, dated Aug. 26, 2020, 10 pages.
International Search Report and Written Opinion for Interantional application No. PCT/US2017/055054, dated Jan. 25, 2018, 14 pages.
International Search Report and Written Opinion for International application No. PCT/GB2007/004073, dated Jan. 31, 2008, 8 pages.
International Search Report and Written Opinion for International application No. PCT/US2017/034814, dated Oct. 11, 2017, 16 pages.
International Search Report and Written Opinion for International application No. PCT/US2017/046508, dated Jan. 17, 2018, 14 pages.
International Search Report and Written Opinion for International application No. PCT/US2017/046737, dated Dec. 14, 2017, 11 pages.
International Search Report and Written Opinion for International application No. PCT/US2017/046777, dated Dec. 13, 2017, 14 pages.
International Search Report and Written Opinion for International application No. PCT/US2018/045155, dated Oct. 15, 2018, 12 pages.
International Search Report and Written Opinion for PCT Application No. PCT/US2022/015985, dated May 30, 2022, 13 pages.
International Search Report and Written Opinion for PCT/US2018/014351, dated Jun. 4, 2018, 9 pages.
International Search Report and Written Opinion for the International Patent Application No. PCT/US2019/035756, datd Jul. 31, 2019, 11 pages.
International Search Report and Written Opinion for the International Patent Application No. PCT/US2019/063615, dated May 3, 2020, 13 pages.
International Search Report and Written Opinion of PCT/US2018/018901, dated Aug. 6, 2018, 12 pages.
International Search Report for International Application No. PCT/US2013/034674, mailed Aug. 6, 2013, 4 pages.
International Search Report for the International Patent Application No. PCT/US03/16640, dated Oct. 2, 2003, 1 page.
International Written Opinion for International Application No. PCT/US2013/034674, mailed Aug. 6, 2013, 13 pages.
Invitation to Pay Additional Fees for International Application No. PCT/US2013/034674, mailed on Jun. 3, 2013, 2 pages.
Notice of Allowance dated Mar. 25, 2016, issued in U.S. Appl. No. 13/854,456, 9 pages.
Notice of Allowance dated May 21, 2018, issued in U.S. Appl. No. 13/854,463, 9 pages.
Notice of Allowance dated May 23, 2018, issued in U.S. Appl. No. 13/854,445, 8 pages.
Office Action dated May 31, 2016, issued in U.S. Appl. No. 13/854,463, 15 pages.
Schott web-page image from Jul. 9, 2016, https://www.us.schott.com/pharmaceutical_packaging/english/products/cartrid es.html.
U.S. Office Action dated Aug. 4, 2015, issued in U.S. Appl. No. 13/854,463, 10 pages.
U.S. Office Action dated Jan. 25, 2017, issued in U.S. Appl. No. 13/854,445, 22 pages.
Schott web-page image from Jul. 9, 2016, https://www.us.schott.com/pharmaceutical_packaging/english/products/cartridges.html.
Author unknown, CeramTec "Discover the Electro Ceramic Products CeramTec acquired from Morgan AdvancedMaterials" [online], Mar. 1, 2001 [retrieved on Jan. 8, 2019. Retrieved from the Internet URL: http://www.morgantechnicalceramics.com/].
Web-Site Brochure dated Dec. 20, 1999. "The Animas R-1000 Insulin Pump", http://www.animascorp.com/pump_f_s.html.
Web-Site Brochure dated Jan. 4, 2000. MiniMed 508. "Doing its job. Naturally." http://www.minimed.com/files/mm113.htm.
Web-Site Brochure dated Jan. 4, 2000. SOOIL-Homepage. "Portable Insulin Pump", http://www.sooil.com/product2.htm.
Web-Site Brochure dated Jan. 4, 2000. "The Glucose Sensor".www.animascorp.corn/sensor_f.html.
Irby et al., "Optimization and Application of a Wrap-Spring Clutch to a Dynamic Knee-Ankle-Foot Orthosis", IEEE Transactions on Rehabilitation Engineering, vol. 7, No. 2, Jun. 1999, pp. 130-134.
Sclater et al., "Mechanisms and Mechanical Devices Sourcebook", McGraw-Hill, 2001, 3rd Edition ISBN: 0-07-136169-3.
Sclater et al., "Mechanisms and Mechanical Devices Sourcebook", McGraw-Hill, 2011, 5th edition ISBN: 978-0-07-170441-0.

\* cited by examiner

FLUID DELIVERY DEVICE, TRANSCUTANEOUS ACCESS TOOL AND FLUID DRIVE MECHANISM FOR USE THEREWITH

CROSS-REFERENCE TO RELATED APPLICATIONS

This application is a continuation of U.S. patent application Ser. No. 16/552,492, filed Aug. 27, 2019, now U.S. Pat. No. 11,229,741, issued Jan. 25, 2022, which is a continuation of U.S. patent application Ser. No. 15/226,510, filed Aug. 2, 2016, now U.S. Pat. No. 10,420,883, issued Sep. 24, 2019, which is a continuation of U.S. patent application Ser. No. 13/854,456, filed Apr. 1, 2013, now U.S. Pat. No. 9,402,950, issued Aug. 2, 2016, which is a continuation of PCT Application Serial No. PCT/US13/34674, filed Mar. 29, 2013 and claims the benefit of the filing date of U.S. Provisional Application Ser. No. 61/618,028, filed Mar. 30, 2012, the teachings of each of which are incorporated herein by reference.

TECHNICAL FIELD

The present invention relates to fluid delivery devices for delivering therapeutic liquids to a patient, and more particularly, to an infusion pump for delivering therapeutic liquids to a patient.

BACKGROUND INFORMATION

Fluid delivery devices have numerous uses such as delivering a liquid medicine or other therapeutic fluid to a patient subcutaneously. In a patient with diabetes mellitus, for example, ambulatory infusion pumps have been used to deliver insulin to a patient. These ambulatory infusion pumps have the ability to offer sophisticated fluid delivery profiles including variable basal rates and bolus requirements. The ability to carefully control drug delivery can result in better efficacy of the drug and therapy and less toxicity to the patient.

Some existing ambulatory infusion pumps include a reservoir to contain the liquid medicine and use electromechanical pumping or metering technology to deliver the liquid medicine via tubing to a needle and/or soft cannula that is inserted subcutaneously into the patient. These existing devices allow control and programming via electromechanical buttons or switches located on the housing of the device. The devices include visual feedback via text or graphic screens and may include alert or warning lights and audio or vibration signals and alarms. Such devices are typically worn in a harness or pocket or strapped to the body of the patient.

Some infusion pumps have been designed to be relatively small, low cost, light-weight, and easy-to-use. One example of such a pump is the OMNIPOD® insulin infusion pump available from Insulet Corporation. Examples of infusion pumps are also described in greater detail, for example, in U.S. Pat. Nos. 7,128,727; 7,018,360; and 7,144,384 and U.S. Patent Application Publication Nos. 2007/0118405, 2006/0282290, 2005/0238507, and 2004/0010207, which are fully incorporated herein by reference. These pumps include insertion mechanisms for causing a transcutaneous access tool, such as a needle and/or soft cannula, to be inserted into a patient. Although such pumps are effective and provide significant advantages over other insulin infusion pumps, the design of the insertion mechanism may be improved, for example, to reduce the size of the pump, to improve the comfort to the user, and/or to incorporate continuous glucose monitoring (CGM). These pumps also include fluid driving mechanisms for driving fluid from a reservoir through the transcutaneous access tool. The fluid driving mechanisms may also be improved to facilitate assembly and use of the pump.

SUMMARY

The present disclosure provides various fluid delivery devices to deliver a liquid medicine or other therapeutic fluid to a patient subcutaneously. In certain embodiments the fluid delivery device may comprise an ambulatory insulin infusion device to administer insulin to a patient. The fluid delivery device may include one or more batteries for providing a power source, a fluid reservoir for holding a fluid, a fluid drive mechanism for driving the fluid out of the reservoir, a fluid passage mechanism for receiving the fluid from the reservoir and passing the fluid to a destination via a transcutaneous access tool, and a transcutaneous access tool insertion mechanism for deploying the transcutaneous access tool.

In certain embodiments, the drive mechanism may comprise a clutch mechanism. As explained herein, by using a clutch mechanism, the number of fluid path prime pulses to prime the pump may be reduced and a full and proper priming of the fluid path before placement on the body may be better assured. The clutch mechanism may also be made suitable for other drug applications without significant redesign, and be more easily inspected than conventional drive mechanisms for infusion devices.

In certain embodiments, the fluid delivery device may comprise a fluid reservoir; a transcutaneous access tool fluidly coupled to the fluid reservoir; and a drive mechanism for driving fluid from the reservoir. The drive mechanism may comprise a plunger received in the reservoir; a leadscrew extending from the plunger; a nut threadably engaged with the leadscrew; a drive wheel; and a clutch mechanism coupled to the drive wheel, wherein the clutch mechanism is configured to allow the nut to pass through the clutch mechanism when disengaged and is configured to grip the nut when engaged such that the drive wheel rotates the nut to advance the leadscrew and the plunger into the reservoir.

In certain embodiments, the fluid delivery device may comprise a fluid reservoir; a transcutaneous access tool fluidly coupled to the fluid reservoir; and a drive mechanism for driving fluid from the reservoir The drive mechanism may comprise a plunger received in the reservoir; an elongated assembly comprising a first elongated member and a second elongated member; the first elongated member extending from the plunger; the second elongated member coupled to the first elongated member; a drive wheel; and a clutch mechanism coupled to the drive wheel, wherein the clutch mechanism is configured to allow the second elongated member to pass through when disengaged and is configured to grip the second elongated member when engaged such that the drive wheel rotates the second elongated member to advance the first elongated member and the plunger into the reservoir.

In certain embodiments, a method of operating a foregoing fluid delivery device may comprise providing the fluid delivery device; holding the clutch mechanism in a disengaged position; filling the fluid reservoir with fluid; passing the second elongated member through the clutch mechanism such that the plunger is retracted within the reservoir;

releasing the clutch mechanism from the disengaged position; and engaging the clutch mechanism with the second elongated member.

BRIEF DESCRIPTION OF THE DRAWINGS

These and other features and advantages will be better understood by reading the following detailed description, taken together with the drawings wherein.

DETAILED DESCRIPTION

Figure 1:
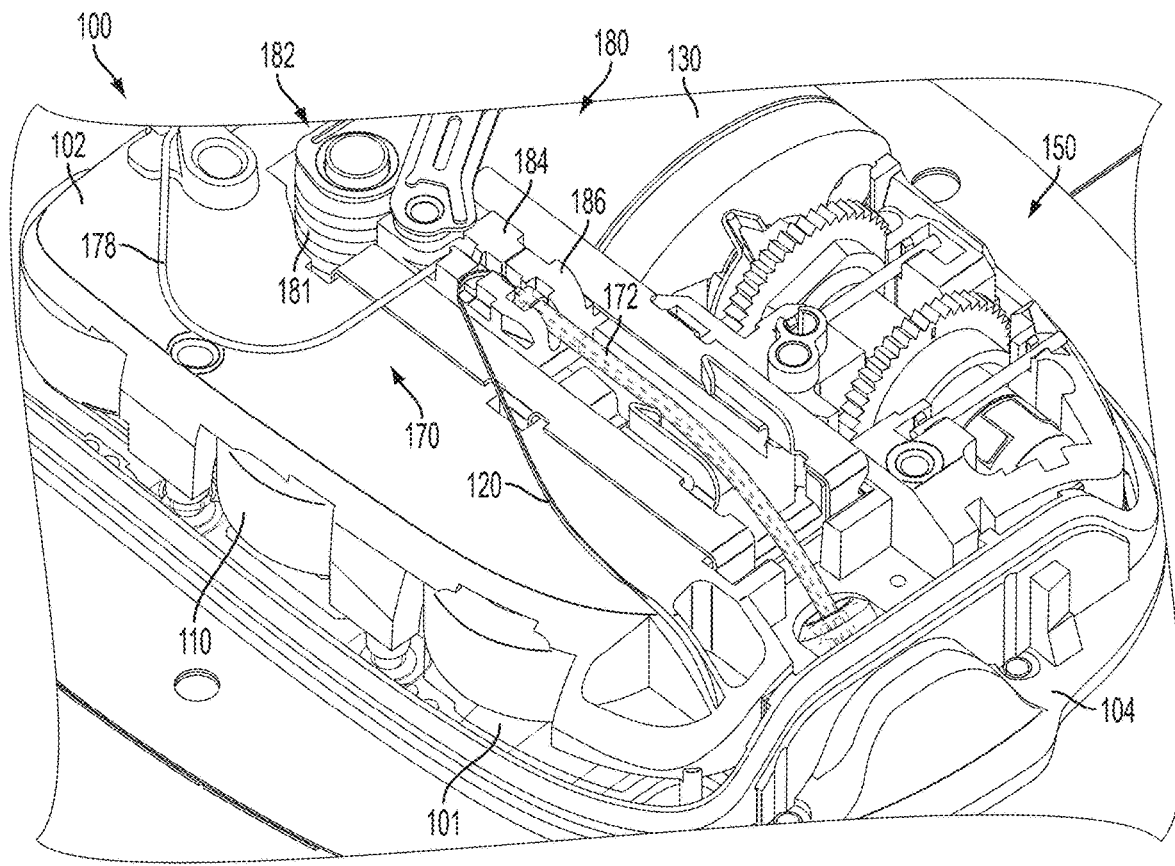
FIG. 1 is a top perspective view of a fluid delivery device with a transcutaneous access tool insertion mechanism in a pre-deployment position, consistent with the present disclosure.
Figure 2:
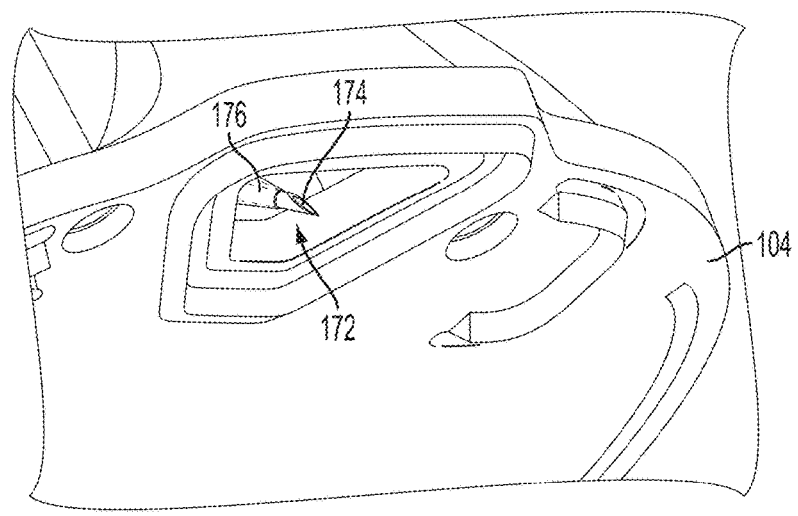
FIG. 2 is a bottom perspective view of a needle and cannula retracted into the fluid delivery device in the pre-deployment position shown in FIG. 1.
Figure 3:
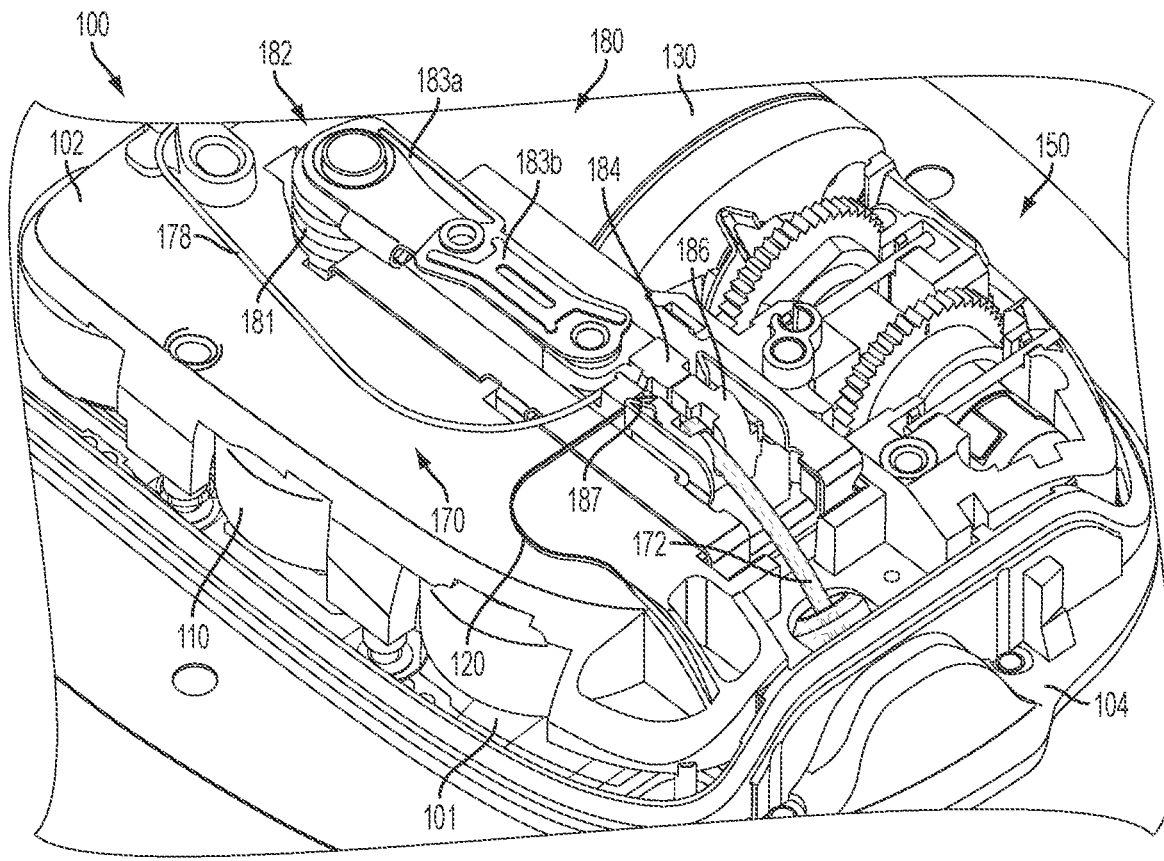
FIG. 3 is a top perspective view of the fluid delivery device shown in FIG. 1 with the insertion mechanism in an intermediate position.
Figure 4:
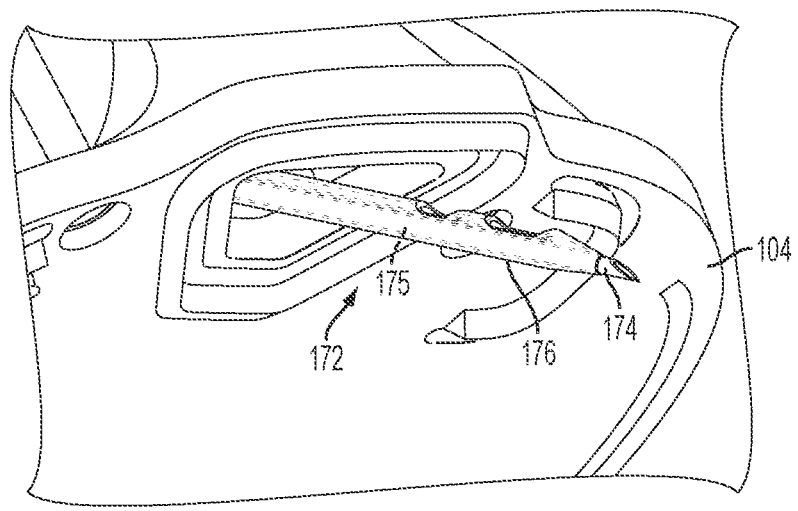
FIG. 4 is a bottom perspective view of the needle and cannula extending from the fluid delivery device in the intermediate position shown in FIG. 3.
Figure 5:
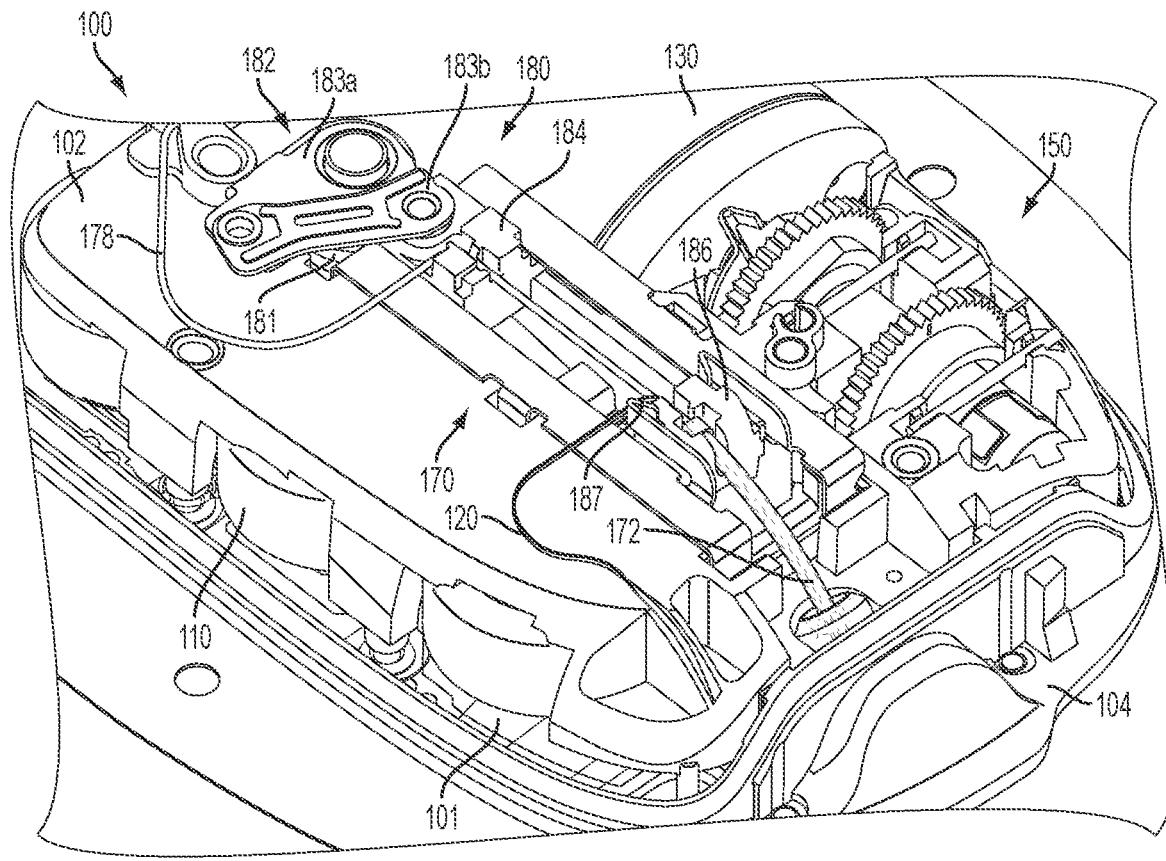
FIG. 5 is a top perspective view of the fluid delivery device shown in FIG. 1 with the insertion mechanism in a post-deployment position.

A fluid delivery device, consistent with embodiments of the present disclosure, may be used to deliver a therapeutic fluid (e.g. a liquid medicine) to a patient via a transcutaneous access tool, such as a needle/trocar and/or a cannula. A transcutaneous access tool insertion mechanism may be used to deploy the transcutaneous access tool, for example, by inserting and retracting a needle/trocar in a single, uninterrupted motion. The insertion mechanism may also provide an increasing insertion force as the needle/trocar moves in the insertion direction. The fluid delivery device may also include a clutch mechanism to facilitate filling a reservoir and engagement of a drive mechanism for driving fluid out of the reservoir. In certain embodiments, the fluid delivery device may comprise an ambulatory insulin infusion device.

In other embodiments, a fluid delivery device may be used to deliver a therapeutic fluid to a patient with integrated monitoring, such as continuous glucose monitoring (CGM). In these embodiments, the fluid deliver device may include a transcutaneous access tool configured to introduce a monitoring test strip through the skin of the patient, for example, using one or more needles, cannulas and/or trocars.

Referring to FIGS. 1-6, one embodiment of a fluid delivery device 100 is shown and described. In the exemplary embodiment, the fluid delivery device 100 is used to subcutaneously deliver a fluid, such as a liquid medicine (e.g. insulin), to a person or an animal. Those skilled in the art will recognize that the fluid delivery device 100 may be used to deliver other types of fluids. The fluid delivery device 100 may be used to deliver fluids in a controlled manner, for example, according to fluid delivery profiles accomplishing bolus requirements, continuous infusion and variable flow rate delivery.

According to one embodiment, the fluid delivery device 100 may include one or more batteries 110 for providing a power source, a fluid reservoir 130 for holding a fluid, a fluid drive mechanism 150 for driving the fluid out of the reservoir 130, a fluid passage mechanism 170 for receiving the fluid from the reservoir 130 and passing the fluid to a destination via a transcutaneous access tool 172, and a transcutaneous access tool insertion mechanism 180 for deploying the transcutaneous access tool 172. The fluid delivery device 100 may include a circuit board 101 with control circuitry for controlling the device and a chassis 102 that provides mechanical and/or electrical connections between components of the fluid delivery device 100. The fluid delivery device 100 may also include a housing 104 to enclose the circuit board 101, the chassis 102, and the components 110, 130, 150, 170, 180.

The fluid delivery device 100 may also include integrated monitoring such as continuous glucose monitoring (CGM). A monitor test strip 120 coupled to a monitor (not shown) in the fluid delivery device 100 may be introduced by the transcutaneous access tool 172 subcutaneously. One example of the monitor test strip is a CGM test strip (such as the type available from Nova Biomedical) which may be understood as a glucose sensor configured to test for a concentration level of glucose in the blood of a patient. The fluid delivery device 100 may be configured to receive data from the monitoring test strip concerning a glucose level of the patient, and determining an output of insulin from the reservoir based on the glucose level.

The transcutaneous access tool 172 includes an introducer needle/trocar 174 at least partially positioned within a lumen 175 of a cannula 176 (e.g., a soft flexible cannula), which is capable of passing the fluid into the patient. In particular, the introducer needle/trocar 174 may initially penetrate the skin such that both the introducer needle/trocar 174 and the cannula 176 are introduced (inserted) into the patient, and the introducer needle/trocar 174 may then be retracted within the cannula 176 such that the cannula 176 remains inserted. A fluid path, such as tubing 178, fluidly couples the reservoir 130 to the lumen 175 of cannula 176 of the transcutaneous access tool 172.

Figure 6:
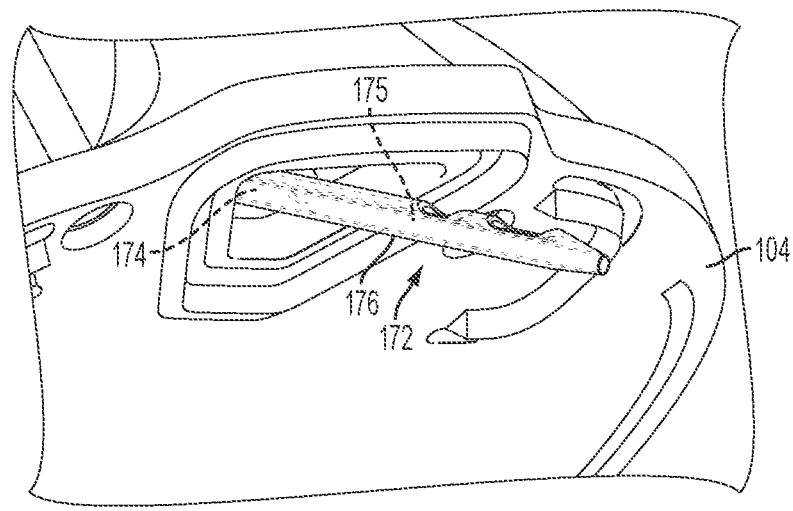
FIG. 6 is a bottom perspective view of the cannula extending from the fluid delivery device in the post-deployment position shown in FIG. 5.

The transcutaneous access tool insertion mechanism 180 is coupled to the transcutaneous access tool 172 to deploy the transcutaneous access tool 172, for example, by inserting the needle/trocar 174 and cannula 176 through the skin of a patient and retracting the needle/trocar 174. In the illustrated embodiment, the insertion mechanism 180 includes a spring-biased linkage mechanism 182 and sliding members 184, 186 coupled to the needle/trocar 174 and cannula 176, respectively, for moving the needle/trocar 174 and cannula 176 in the insertion direction and for moving the needle/trocar 174 in the retraction direction. In a single, uninterrupted motion, the spring-biased linkage mechanism 182 moves from a pre-deployment position (FIG. 1) with both needle/trocar 174 and cannula 176 retracted (FIG. 2) to an intermediate position (FIG. 3) with both needle/trocar 174 and cannula 176 inserted (FIG. 4) to a post-deployment position (FIG. 5) with the needle/trocar 174 retracted and the cannula 176 inserted (FIG. 6).

Referring to FIGS. 7-12, one embodiment of the fluid drive mechanism 150 uses a clutch mechanism 160 to facilitate filling of the reservoir 130 and engagement of the fluid drive mechanism 150 for driving fluid out of the reservoir 130. The fluid drive mechanism 150 includes a first threaded member in the form of an elongated shaft such as a threaded drive rod or leadscrew 152, with external threads extending from a plunger 136 received in the reservoir 130 and sealed with an o-ring 137 against the inside surface of the reservoir 130. The leadscrew 152 and plunger 136 may be an inseparable, insert-molded assembly. A second threaded member in the form of an elongated shaft such as a tube nut 154 with internal threads threadably engages the leadscrew 152 and may be driven by a drive wheel 156 via a clutch mechanism 160.

When the reservoir 130 is empty (FIGS. 7 and 8), the plunger 136 is positioned at one end of the reservoir 130 such that the plunger 136 is extended and the clutch mechanism 160 is disengaged. In certain embodiments, the reservoir 130 may be filled with fluid, particularly insulin, by opening an inlet port to the reservoir 130 and pumping in the insulin under sufficient hydraulic pressure to retract the plunger 136 within the reservoir 130. Thereafter, the inlet port may be closed. When the reservoir 130 is filled and the plunger 136 moves to the opposite (retracted) end of the reservoir 130 (FIG. 9), the clutch mechanism 160 remains disengaged to allow the tube nut 154 to pass into an elongated cylindrical bore (along the drive axis) of a hub of the drive wheel 156. The clutch mechanism 160 may then be engaged (FIGS. 10-12) such that rotation of the drive wheel 156 causes the clutch mechanism 160 to rotate the tube nut 154, which causes the leadscrew 152 to advance the plunger into the reservoir 130 to deliver the fluid from the reservoir 130. In alternative embodiments, the reservoir 130 may be filled when the plunger 136 is already retracted.

Figure 7:
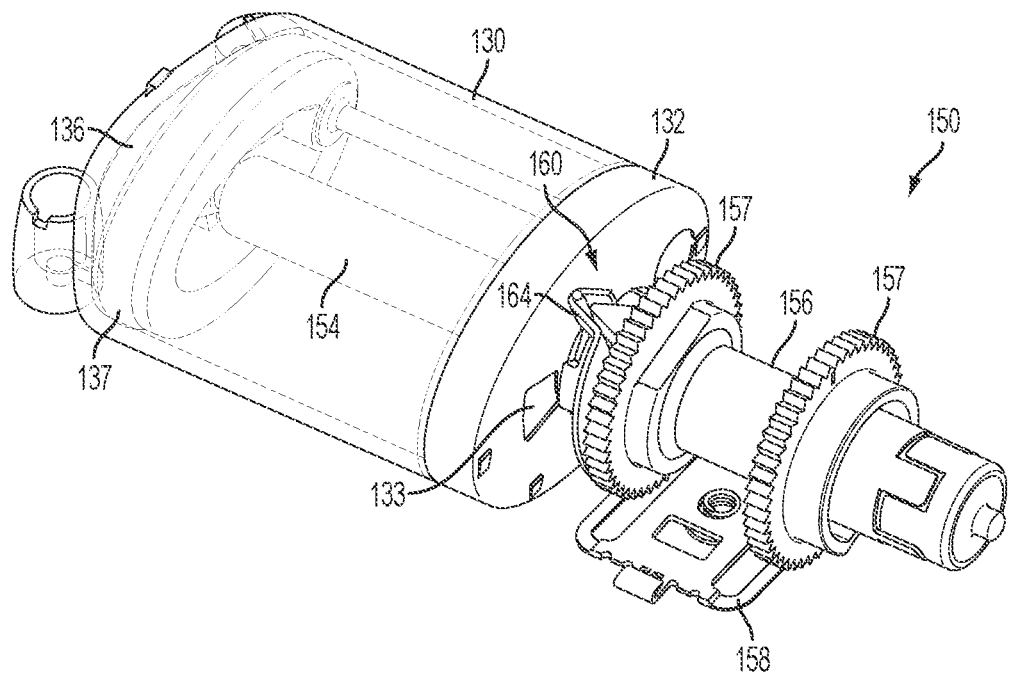
FIG. 7 is a top perspective view of a fluid driving mechanism of the fluid delivery device shown in FIG. 1 with a clutch mechanism in a disengaged position prior to filling.
Figure 8:
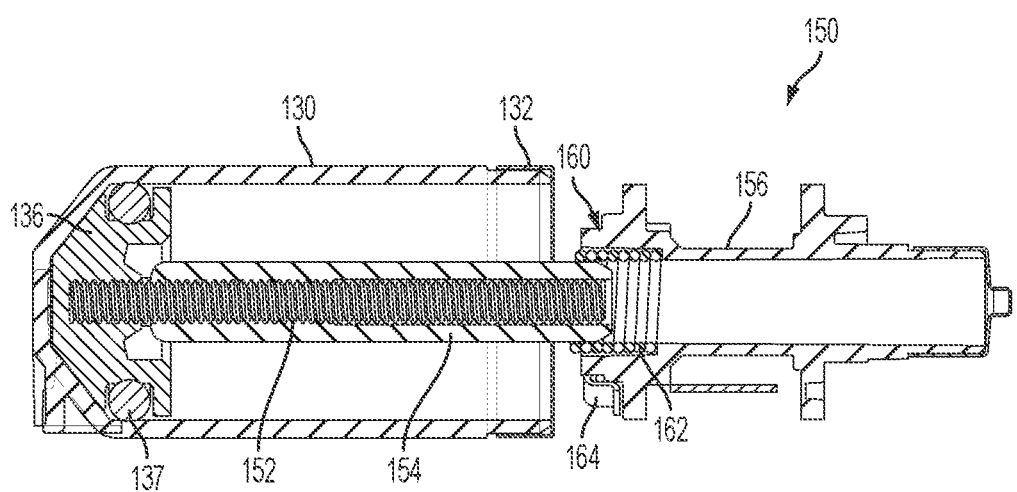
FIG. 8 is a side cross-sectional view of the fluid driving mechanism shown in FIG. 7.
Figure 9:
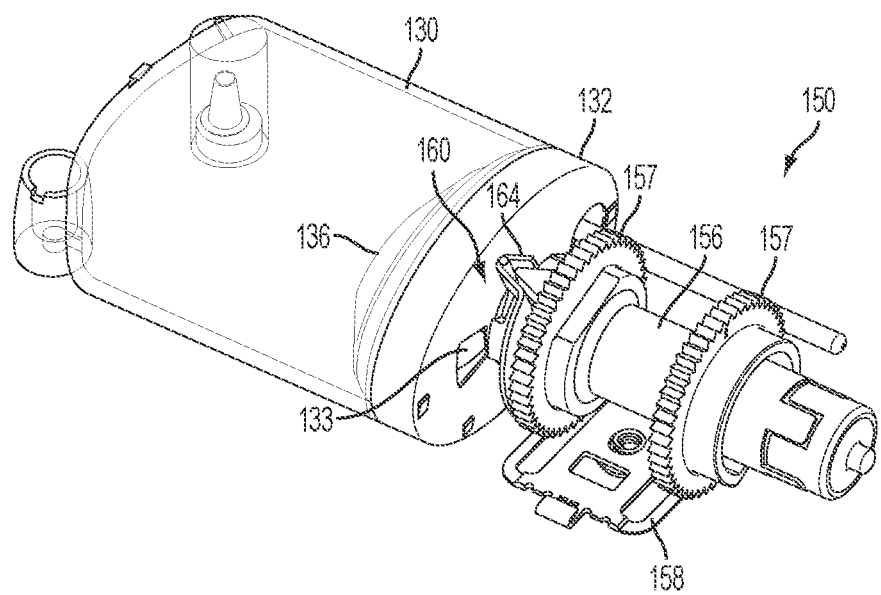
FIG. 9 is a top perspective view of the fluid driving mechanism shown in FIG. 7 with the clutch mechanism in a disengaged position after filling.
Figure 10:
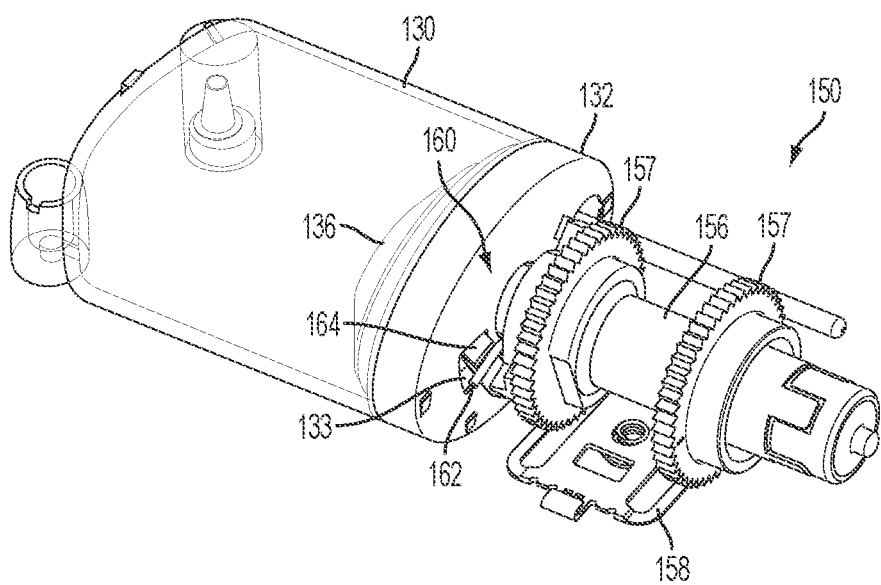
FIG. 10 is a top perspective view of the fluid driving mechanism shown in FIG. 7 with the clutch mechanism being released to the engaged position.
Figure 11:
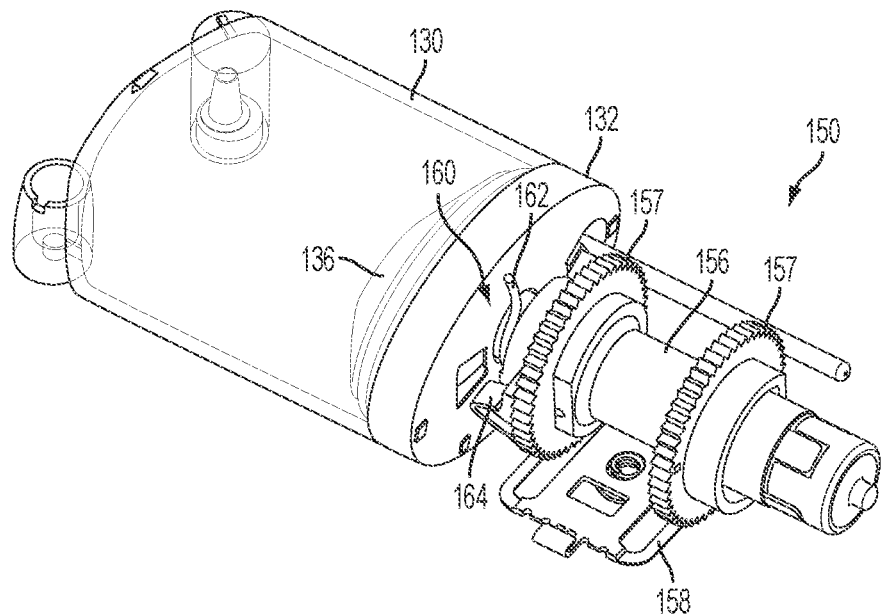
FIGS. 11 and 12 are top perspective views of the fluid driving mechanism shown in FIG. 7 with the clutch mechanism in the engaged position.
Figure 12:
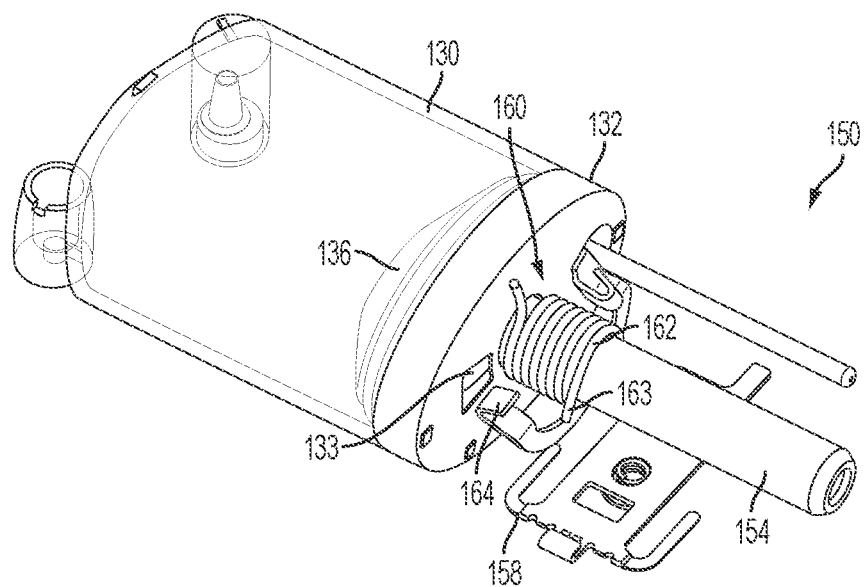

In the illustrated embodiment, the clutch mechanism 160 includes a clutch spring 162 (e.g., a helical torsion spring) located in a counterbore at one end of the drive wheel 156, adjacent the reservoir 130. The inside diameter of the clutch spring 162 is larger than the outside diameter of the tube nut 154 when the clutch spring 162 is loaded, thereby disengaging the clutch spring 162 from the tube nut 154 and allowing the tube nut 154 to pass through the center aperture of the clutch spring 162 and into the elongated bore of the drive wheel 156. Alternatively, the inside diameter of the clutch spring 162 is smaller than the outside diameter of the tube nut 154 when the clutch spring 162 is unloaded, thereby engaging or gripping the tube nut 154 and allowing the drive wheel 156 to rotate the tube nut 154. In the illustrated embodiment, prior to filing the reservoir 130, the clutch spring 162 is held in the loaded, disengaged position by a spring latch 164 engaged with the drive wheel 156 (FIGS. 7-9). After the reservoir 130 has been filled, the clutch spring 162 may thus be engaged by rotating the drive wheel 156 until the spring latch 164 releases the clutch spring 162 (FIG. 10) allowing the clutch spring 162 to unload and grip the tube nut 154 (FIGS. 11 and 12), at which time fluid may be dispensed from the reservoir 130 with continued rotation of the drive wheel 156.

As shown, the spring latch 164 may be biased by the clutch spring 162 such that as the drive wheel 156 rotates the spring latch 164 moves rotationally against a surface of a reservoir cap 132 until clutch spring 162 deflects the spring latch 164 into a window 133 in the reservoir cap 132. When the spring latch 164 moves into the window 133, the end of the clutch spring 162 held by the spring latch 164 is released, thus engaging the clutch mechanism 160. When the clutch spring 162 is engaged, the drive wheel 156 contacts an end 163 of the clutch spring 162 to create a thrust on the clutch spring 162 that causes the clutch spring 162 to rotate the tube nut 154. The fluid drive mechanism 150 may also use other clutch mechanisms capable of allowing the tube nut 154 or other type of nut or threaded member to pass through the clutch mechanism and then being activated to engage the nut or threaded member.

In the illustrated embodiment, the drive wheel 156 includes ratchets 157 that are engaged by an actuator 158 to incrementally drive the wheel 156 and advance the plunger 136 into the reservoir 130. Examples of this actuation mechanism are described in greater detail in U.S. Patent Application Publication No. 2005/0238507, which is fully incorporated herein by reference.

By using a clutch mechanism, the engagement between the leadscrew and the nut occurs at assembly, and thus no rotation is needed for the nut to engage the leadscrew by operation of the device. This reduces the number of fluid path prime pulses to prime the pump and assures a full and proper priming of the fluid path before placement on the body. The clutch mechanism also enables the changing of thread pitch for other drug applications without a need to redesign the tilt nut used in fluid driving mechanisms in other existing pumps. The components of the clutch mechanism are also more easily inspected than the tilt nut assembly.

While the principles of the invention have been described herein, it is to be understood by those skilled in the art that this description is made only by way of example and not as a limitation as to the scope of the invention. Other embodiments are contemplated within the scope of the present invention in addition to the exemplary embodiments shown and described herein. Modifications and substitutions by one of ordinary skill in the art are considered to be within the scope of the present invention, which is not to be limited except by the following claims.

What is claimed is:

1. A drive mechanism for a fluid delivery device, comprising:
   a plunger disposed within a reservoir;
   a leadscrew extending from the plunger;
   a nut threadably engaged with the leadscrew;
   a drive wheel; and
   a clutch mechanism coupled to the drive wheel, wherein the clutch mechanism is configured to allow the nut to pass through the clutch mechanism when disengaged and is configured to grip the nut when engaged such that the drive wheel rotates the nut to advance the leadscrew and the plunger into the reservoir.

2. The drive mechanism of claim 1, wherein the nut is a tube nut.

3. The drive mechanism of claim 2, wherein the clutch mechanism includes a clutch spring that grips the tube nut when the clutch spring is released.

4. The drive mechanism of claim 1, wherein the clutch mechanism further includes a spring latch and a clutch spring, and the spring latch is operable to hold the clutch spring in a disengaged position and to release the clutch spring such that the clutch spring moves to an engaged position.

5. The drive mechanism of claim 4, wherein the spring latch is configured to release the clutch spring in response to movement of the drive wheel.

6. A drive mechanism for a fluid delivery device, comprising:
an elongated assembly including a first elongated member and a second elongated member, wherein the first elongated member is configured to extend from a plunger within a reservoir and the second elongated member is coupled to the first elongated member;
a drive wheel; and
a clutch mechanism coupled to the drive wheel, wherein the clutch mechanism is configured to allow the second elongated member to pass through the clutch mechanism when disengaged and is configured to grip the second elongated member when engaged such that the drive wheel rotates the second elongated member to advance the first elongated member and the plunger into the reservoir.

7. The drive mechanism of claim 6, wherein:
the first elongated member comprises a first threaded member;
the second elongated member comprises a second threaded member; and
the second threaded member is in threaded engagement with the first threaded member.

8. The drive mechanism of claim 7, wherein the first threaded member comprises a first threaded shaft having external threads.

9. The drive mechanism of claim 7, wherein the second elongated member comprises a second threaded shaft having internal threads.

10. The drive mechanism of claim 6, wherein the clutch mechanism includes a clutch spring that grips the second elongated member when released.

11. The drive mechanism of claim 10, wherein the clutch mechanism further includes a spring latch configured to hold the clutch spring in a disengaged position and configured to release the clutch spring such that the clutch spring moves to an engaged position.

12. The drive mechanism of claim 11, wherein the spring latch is configured to release the clutch spring in response to movement of the drive wheel.

13. A fluid delivery device, comprising:
a fluid reservoir;
a transcutaneous access tool fluidly coupled to the fluid reservoir; and
a drive mechanism including an elongated assembly coupled to a plunger disposed in the fluid reservoir and a clutch mechanism, wherein the drive mechanism is operable to:
hold the clutch mechanism in a disengaged position;
as the fluid reservoir is filled with fluid, enable a portion of the elongated assembly to pass through the clutch mechanism such that the plunger is retracted within the fluid reservoir; and
engage the clutch mechanism to hold the portion of the elongated assembly that has passed through the clutch mechanism.

14. The fluid delivery device of claim 13, wherein the drive mechanism is further operable to:
hold the clutch mechanism in the disengaged position while the fluid reservoir is filling with fluid.

15. The fluid delivery device of claim 13, wherein the clutch mechanism comprises a clutch spring operable to hold the portion of the portion of the elongated assembly that passes through the clutch spring of the clutch mechanism.

16. The fluid delivery device of claim 15, wherein the clutch mechanism further comprises a spring latch; and the spring latch is operable to:
hold the clutch mechanism in a disengaged position.

17. The fluid delivery device of claim 16, wherein the drive mechanism, when engaging the clutch spring, is further operable to:
release the clutch spring from the spring latch.

18. The fluid delivery device of claim 13, wherein the elongated assembly comprises:
a first elongated member including a first threaded member; and
a second elongated member includes a second threaded member, wherein the second threaded member is in threaded engagement with the first threaded member; and the clutch mechanism is configured to allow the second threaded member to pass through when disengaged and is configured to grip the second threaded member when engaged, wherein the second threaded member is the portion of the elongated assembly.

19. The fluid delivery device of claim 18, wherein drive mechanism is further operable to:
rotate the second threaded member by rotating a drive wheel with the clutch mechanism engaged whereby the first threaded member and the plunger are advanced into the reservoir.

20. The fluid delivery device of claim 18, wherein the clutch mechanism comprises a clutch spring, and the clutch mechanism, when engaged, is operable to:
grip the second elongated member with the clutch spring.

* * * * *